(12) United States Patent
Aumuller

(10) Patent No.: US 6,309,217 B1
(45) Date of Patent: Oct. 30, 2001

(54) DENTAL ABRADING TOOL

(75) Inventor: Paul M. Aumuller, Richmond Hill (CA)

(73) Assignees: Ardem Inc.; Donald Kramer, both of Toronto (CA)

( * ) Notice: Subject to any disclaimer, the term of this patent is extended or adjusted under 35 U.S.C. 154(b) by 0 days.

(21) Appl. No.: 09/419,478

(22) Filed: Oct. 15, 1999

Related U.S. Application Data

(60) Provisional application No. 60/104,354, filed on Oct. 15, 1998.

(51) Int. Cl.[7] ................................................ A61C 3/02
(52) U.S. Cl. ................................................ 433/88
(58) Field of Search .......................... 433/88, 80, 115, 433/116

(56) References Cited

U.S. PATENT DOCUMENTS

| | | | |
|---|---|---|---|
| 2,324,250 | * | 7/1943 | Voerge . |
| 2,669,809 | * | 2/1954 | McGrath . |
| 2,696,049 | | 12/1954 | Black . |
| 3,972,123 | * | 8/1976 | Black . |
| 4,173,977 | | 11/1979 | Burns . |
| 4,174,571 | * | 11/1979 | Gallant ................................. 433/88 |
| 4,412,402 | * | 11/1983 | Gallant ................................. 433/88 |
| 4,492,571 | | 1/1985 | Warrin . |
| 4,676,749 | * | 6/1987 | Mabille ................................ 433/88 |
| 4,696,644 | * | 9/1987 | Goof .................................... 433/88 |
| 4,950,160 | * | 8/1990 | Karst ................................... 433/88 |
| 4,984,984 | * | 1/1991 | Esrock ................................. 433/88 |
| 5,120,219 | * | 6/1992 | DeFarcy .............................. 433/88 |
| 5,334,019 | * | 8/1994 | Goldsmith et al. ................. 433/88 |
| 5,352,118 | * | 10/1994 | Franetzki et al. .................. 433/82 |
| 5,419,703 | | 5/1995 | Warrin et al. . |
| 5,547,376 | * | 8/1996 | Harrel ................................ 433/116 |
| 5,775,901 | | 7/1998 | Riso . |
| 5,820,373 | * | 10/1998 | Okano et al. ....................... 433/80 |
| 5,897,826 | | 4/1999 | Lashmore et al. . |
| 5,927,977 | | 7/1999 | Sale et al. . |
| 5,967,779 | * | 10/1999 | Brassil et al. . |

FOREIGN PATENT DOCUMENTS

| 298 20 845 U1 | 3/1999 | (DE) . |
|---|---|---|
| 2 624 369 | 6/1989 | (FR) . |

OTHER PUBLICATIONS

Dentsply brochure date unknown.
Dentsply brochure date unknown
Advertisement for Cavitron Prophy–Jet, May 1999, Dental Products Report, p. 3.*

* cited by examiner

Primary Examiner—Ralph A. Lewis
(74) Attorney, Agent, or Firm—Bazerman & Drangel, P.C.

(57) ABSTRACT

A dental abrading tool for use in micro-dentistry that utilizes abrasive dust as the abrasion material, and which provides for effective dust suppression through the use of a water-aerosol spray. The tool consists of a means for the emission of a stream of the abrasive material A spray of water-aerosol is also emitted from the tool in a manner which effectively controls widespread contamination by the emitted abrasive material.

69 Claims, 8 Drawing Sheets

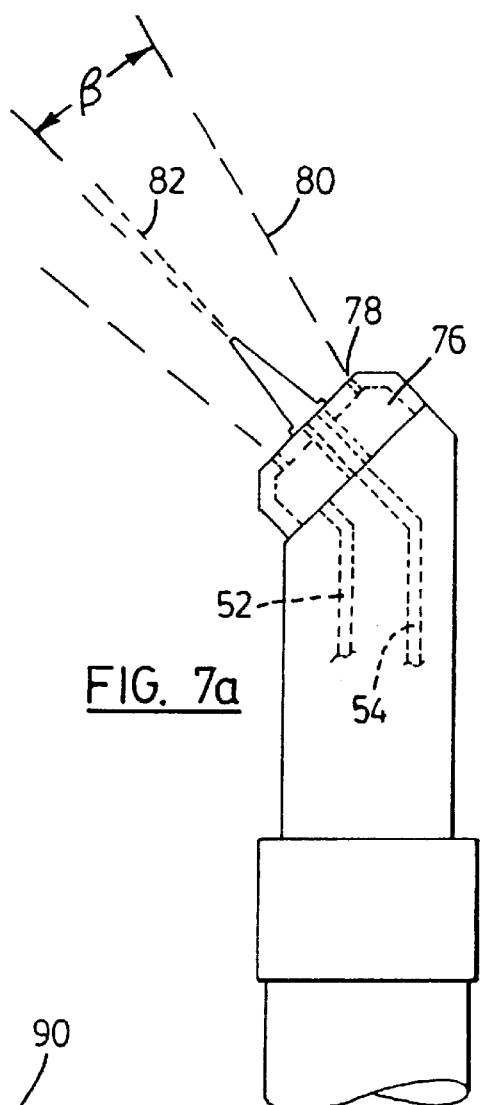
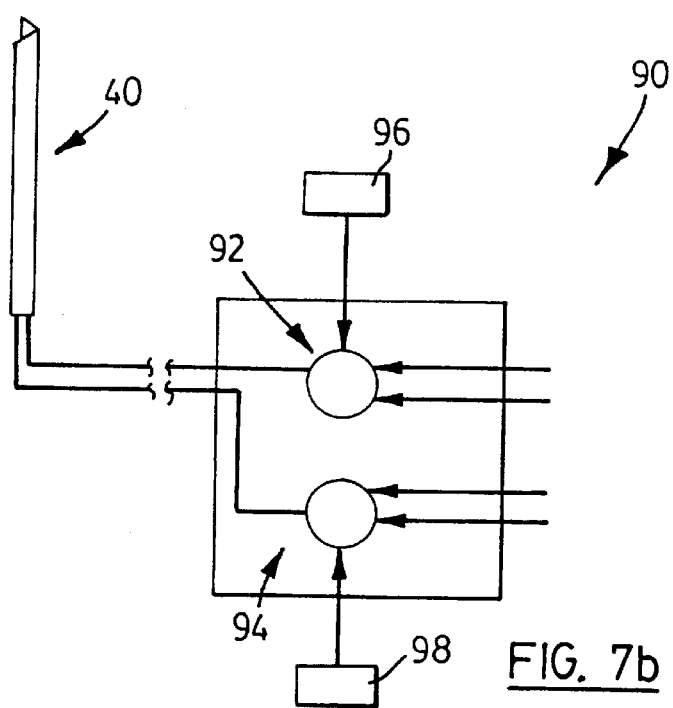
FIG. 7a
FIG. 7b

DENTAL ABRADING TOOL

REFERENCE TO CO-PENDING APPLICATION

The subject matter of U.S. provisional application serial No. 60/104,354 filed Oct. 15, 1998 is incorporated herein by reference.

FIELD OF THE INVENTION

The present invention relates to dental abrasion systems and techniques and more particularly to the control of airborne abrasion materials by way of fluid streams, such as for example a water-aerosol spray.

BACKGROUND OF THE INVENTION

The conventional technique for repairing or otherwise treating teeth in dental procedures such as the removal of caries or in the manufacture/repair of dental prosthetic (eg crowns, dentures) typically involve the use of rotary drills. These drills perform at preset speeds, typically "high or low". As a result, these instruments lack fine control and are imprecise. Furthermore, the drilled surfaces are relatively smooth and are generally not ideal adhesive surfaces for the metals, porcelain, acrylics and/or composites routinely used in dental practice.

As an alternative, the use of air abrasion in microdentistry (AAMD) is attractive Its current but limited use extends to both intra (ie. removal of caries) and extraoral (ie dental prosthetic) applications. A major advantage of AAMD over conventional rotary drills is that it is more precise and affords the user much more control in the aforementioned intra and extraoral applications. Additionally, AAMD typically results in augmented and eroded surface areas which are more amenable to adhesion to metals, porcelain, acrylics and composites. This latter adhesion can be increased by 80% when compared with surfaces resulting from conventional drilling Notwithstanding the apparent advantages of AAMD over conventional rotary drilling, the use of the former has been limited by technical and health-related difficulties. Conventional AAMD devices are not capable of controlling emissions of both the abrasive dust and airborne abraded dental amalgam material, inside the mouth of the patient and outside to the dental operatory. The abrasive material typically includes an aluminum oxide powder of 27.5 to 50.0 microns in particle size and therefore travels easily in ambient air as dust. Its aluminum content makes it a toxicological risk for Alzheimer's Disease. Meanwhile, the abraded dental amalgam can have toxic constituents such as mercury from old dental fillings. This contamination of dental operatories persists in current applications despite the use of high efficiency particulate air (HEPA) vacuum systems. Furthermore, extensive use of intraoral latex rubber dams are also necessary to aid in the prevention of inhaling the respirable aluminum powder by patients. The use of these latter latex rubber dams is also problematic in light of the possibility of inducing latex-associated asthmatic or respiratory type reactions. As neither prevention technique is particularly efficient or effective, the continuance of exposure to the abrasive dust and abraded dental amalgam and the attendant potential for health complication(s) is of concern to both patients and dental professionals.

In light of this prior art, the development of an abrasion system that provides improved dust suppression would be considered revolutionary within the field of micro-dentry As such, overcoming the problem of respirable dust would create better visibility, healthier conditions, make practical extra and intra-oral usage and eliminate the need for costly high efficiency particulate air (HEPA) filter vacuum units.

It is therefore an object of the present invention to provide a novel dental abrasion system It is also an object of the present invention to provide novel techniques for dental abrasion.

SUMMARY OF THE INVENTION

In one aspect of the present invention, there is provided a dental abrasion device comprising first delivery means to deliver pressurized abrasive material to a tooth region and second delivery means to deliver a supply of pressurized fluid near said tooth region under conditions sufficient to suppress airborne emissions of said abrasive material from said tooth region.

Preferably, the first delivery means includes a head and a nozzle mounted on the head with a first conduit therein to receive the abrasive material. The second delivery means includes a plurality of second conduits near the first conduit to receive the pressurized fluid The second conduits are arranged so that the fluid leaving them generates, for example, a curtain-like stream toward the tooth region In other words, the individual fluid streams leaving the second conduits converge to a hollow substantially continuous stream to define an inner region Conveniently, the first conduit may be arranged to deliver the abrasive material to the inner region The pressure and content of the fluid stream can thus retard or, in some cases prevent, airborne abrasive material from breaking through the curtain, either causing it to be entrained in the fluid or to be repelled back into the inner region.

The pressurized fluid may be provided in a variety of forms including a mixture of water and a gas such as air, or other suitable gases such as nontoxic or inert gases, for example nitrogen or carbon dioxide. In the case of air, the fluid may include 10 to 75 percent water by volume, or more preferably 25 to 65 percent water by volume. The pressurized fluid itself may be dispensed, if desired, at pressures ranging from 5 to 75 psi, for example.

In another aspect of the present invention, there is provided a dental abrasion device comprising first delivery means to deliver abrasive material to a tooth region and second delivery means to deliver a supply of pressurized fluid near said tooth region under suitable conditions for retarding the passage of airborne abrasive material there through.

Preferably, the pressurized fluid forms a curtain of fluid around the tooth region More preferably, the curtain completely encircles the tooth region In still another aspect of the present invention, there is provided a dental abrasion system operable to deliver an abrasive material stream to a tooth region and a fluid stream near said tooth region under conditions sufficient to suppress airborne abrasive material emissions from said tooth region In still another aspect of the present invention, there is provided a method of abrading a tooth, comprising the steps of delivering first supply of abrasive material to a tooth region in a patient's oral cavity and delivering a second supply of fluid near said tooth region, wherein said fluid has sufficient volume and pressure to form a barrier to airborne abrasive material between said tooth region and said oral cavity Thus, the invention provides a dental abrading tool that utilizes abrasive dust as the abrasion material, and which provides effective dust suppression by the use of a fluid stream, such as for example a water-aerosol spray. In this example, the tool emits a stream of the abrasive material as well as the water-aerosol spray, the latter under conditions sufficient to minimize the amount of dust leaving the tooth region and thus control widespread contamination by the airborne abrasive material.

For example, the dental abrading tool may be hand controlled, by way of "push botton" or "touch sensory" controls. Furthermore, the controls may be such that the fluid and abrasive streams are continuously variable, are regulated in a stepwise manner (ie high-medium-low), or are controlled in a simple on-off manner. The tool may also be used with a foot pedal or other such control mechanisms The invention may also control the composition of the abrasive material stream and the fluid stream, such as pressure, flow rate, temperature and the like. The tool can also be made adaptable to operatory compressors, and water and electrical supply outlets as allowed by available technology.

BRIEF DESCRIPTION OF THE DRAWINGS

Several preferred embodiments of the present invention will be provided, by way of example only, with reference to the appended drawings, wherein:

FIG. 7a is a magnified view of a portion of the tool of FIG. 6;

FIG. 7b is a schematic view of a dental abrasion system; and

DESCRIPTION OF THE PREFERRED EMBODIMENTS

Figure 1:
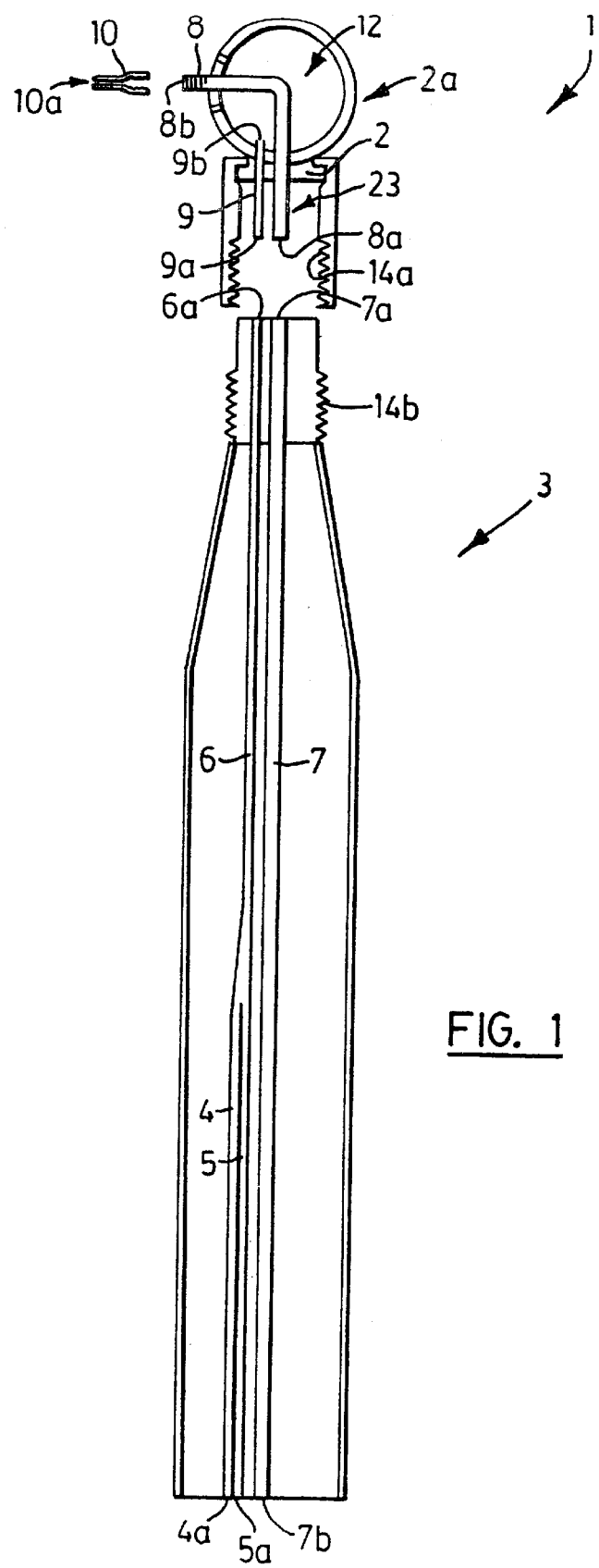
FIG. 1 is a side view of a dental abrading tool.

Referring now to FIG. 1, an abrading tool is shown at 1 having a head section 2 which is removably attached to a body section 3 by a threaded connection shown at 14a and 14b, it being understood that other attachment modes and means are also feasible. The head section 2 defines a cavity 12 into which a water supply tube 9 opens and across which an abrasive material supply tube 8 extends. A detachable nozzle 10 is affixed to a portion of tube 8 that extends outwards from the head section 2.

Body section 3 is an elongated structure containing a sense of tubes 4, 5, 6, and 7 which cross but do not empty internally to body section 3 Tube 7 crosses the entire length of body section 3 and opens externally at either ends of body section 3 at tube openings 7a and 7b Similarly, tubes 4 and 5 open externally to body section 3 at tube openings 4a and 5a respectively At a point distal to these tube openings (ie 4a and 5a) and internal of the body section 3, tubes 4 and 5 merge into a single tube 6. This latter tube 6 opens externally to body section 3 at tube opening 6a. However, it will also be understood that these tubes may be joined at other points both internal and external to the body section For example, an external control portion may be a convenient place to mix the constituents of the pressurized fluid The head section has plate 2a which is retained for swivel movement in the threaded section 14a.

When the head section 2 and the body section 3 are joined or fastened together, tube 9 joins with tube 6 (openings 9a and 6a form a juncture point) and tube 8 joins with tube 7 (openings 8a and 7a form a juncture point) Air may be pumped into tube 4 (through tube opening 4a) and water into tube 5 (through tube opening 5a) or vice versa. The air and water streams are mixed to form a water-aerosol at the point in which tubes 4 and 5 merge, and in tube 6 thereafter. This water-aerosol flows through tube 6, and then tube 9 to empty into cavity 12 Abrasive material is streamed under pressure into tube 7 via opening 7b The abrasive material streams through tube 7 into contiguously joined tube 8 to exit at tube opening 8b.

Figure 2:
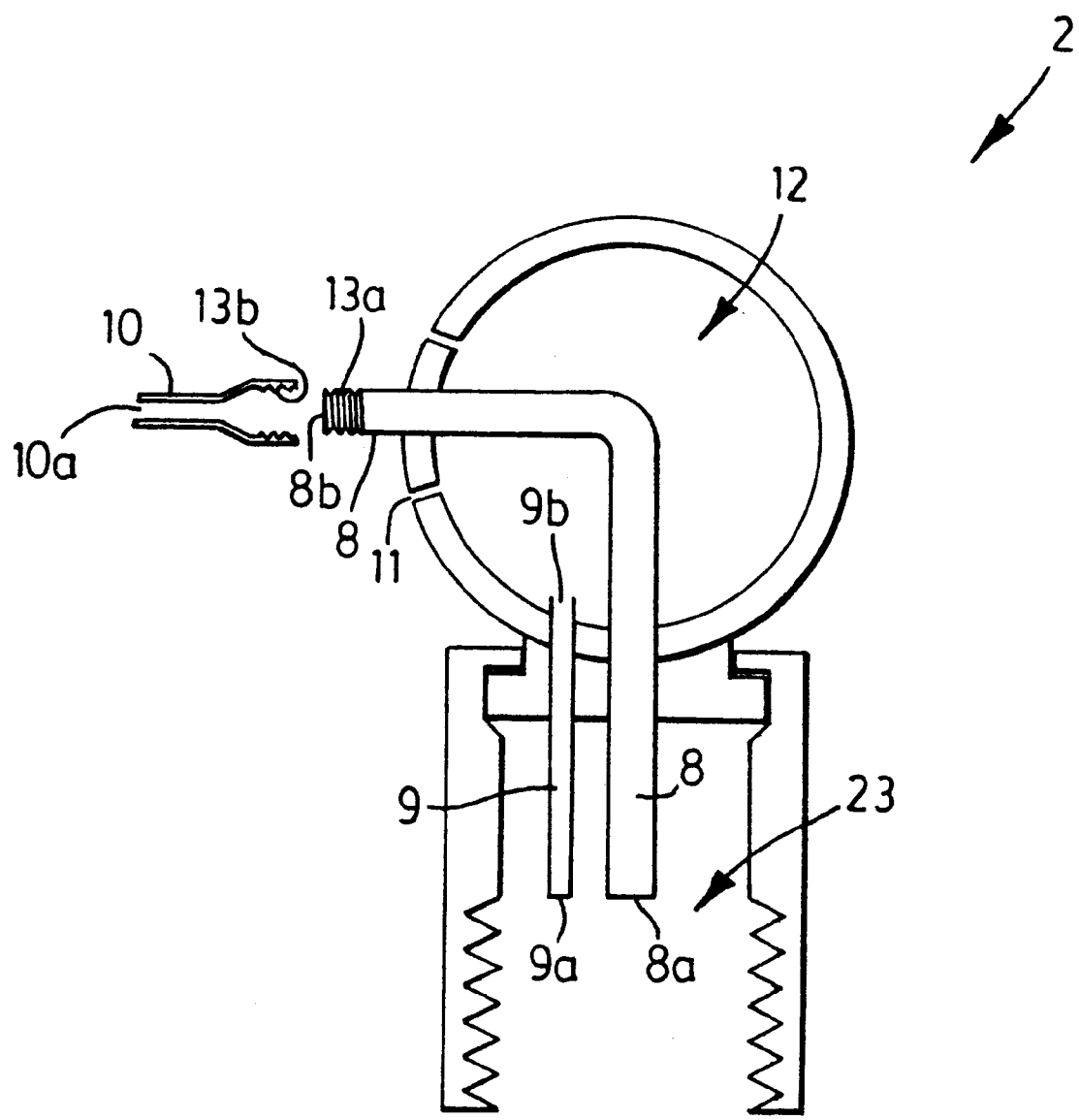
FIG. 2 is magnified side view of one portion of the tool of FIG. 1.
Figure 3A:
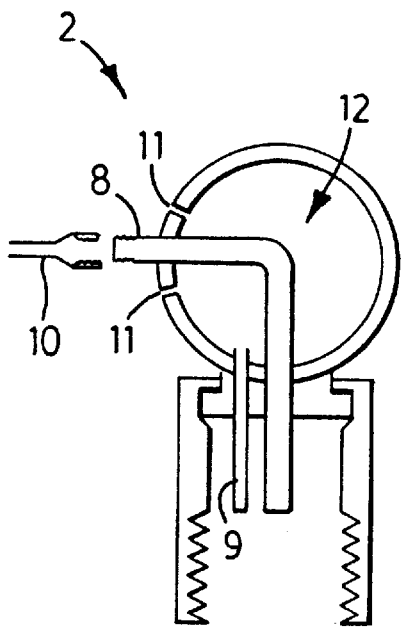
FIGS. 3a to 3d are side views of alternatives to the portion shown in FIG. 2.
Figure 3B:
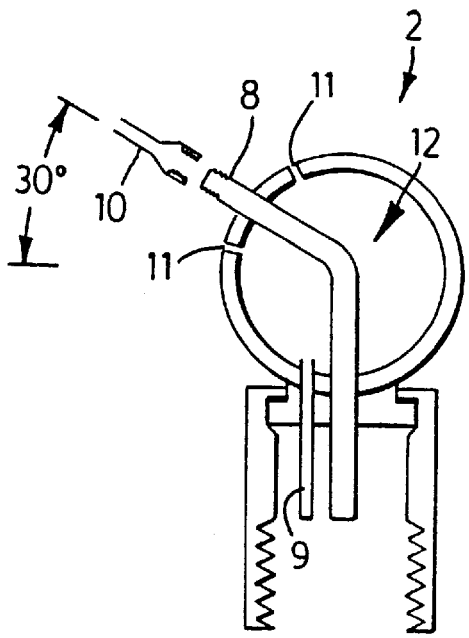
Figure 3D:
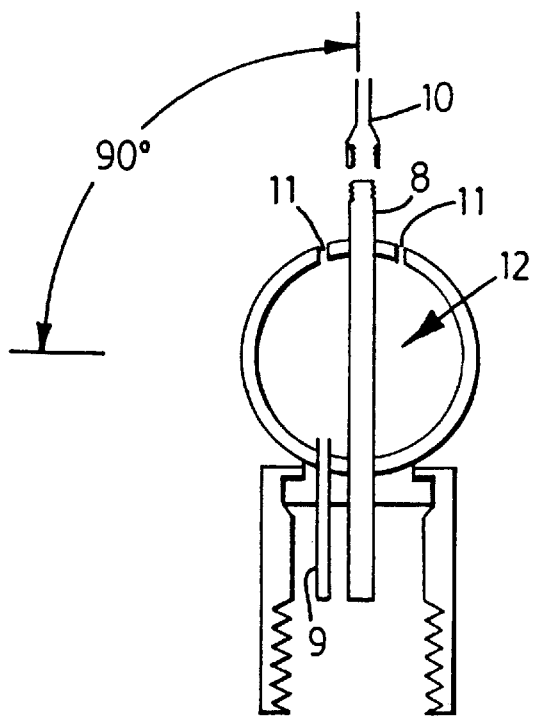
Figure 3C:
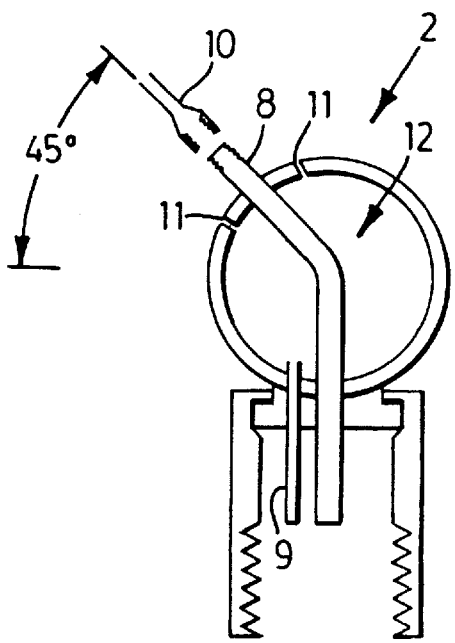

Referring to FIG. 2, a nozzle 10 is further attached to tube 8 via threaded means 13a and 13b, though it will be understood that other attachment modes and means are feasible. Nozzle 10 opens at some external point (10a) to head section 2. This nozzle 10 and its opening 10a can be of various sizes and configurations. As previously noted, abrasive material is streamed under pressure through tube 8, to subsequently exit through opening 10a to nozzle 10 The water-aerosol emptying from tube 9 fills cavity 12 of head section 2. The water-aerosol is channelled through openings 11 of head section 2 to form a water curtain that surrounds nozzle 10 It is the formation of this water curtain that may be configured effectively to control and minimize the widespread contamination of the surroundings by airborne abrasive material emitted through nozzle 10.

FIGS. 3a through 3d show alternatives to the head section 2 in which the fixed angle that tube 9 crosses cavity 12 varies. It should be noted that other embodiments are envisioned in which a swivel hinge or mechanism is incorporated in a single head section 2 thus allowing for the variable adjustment of this angle.

Figure 4:
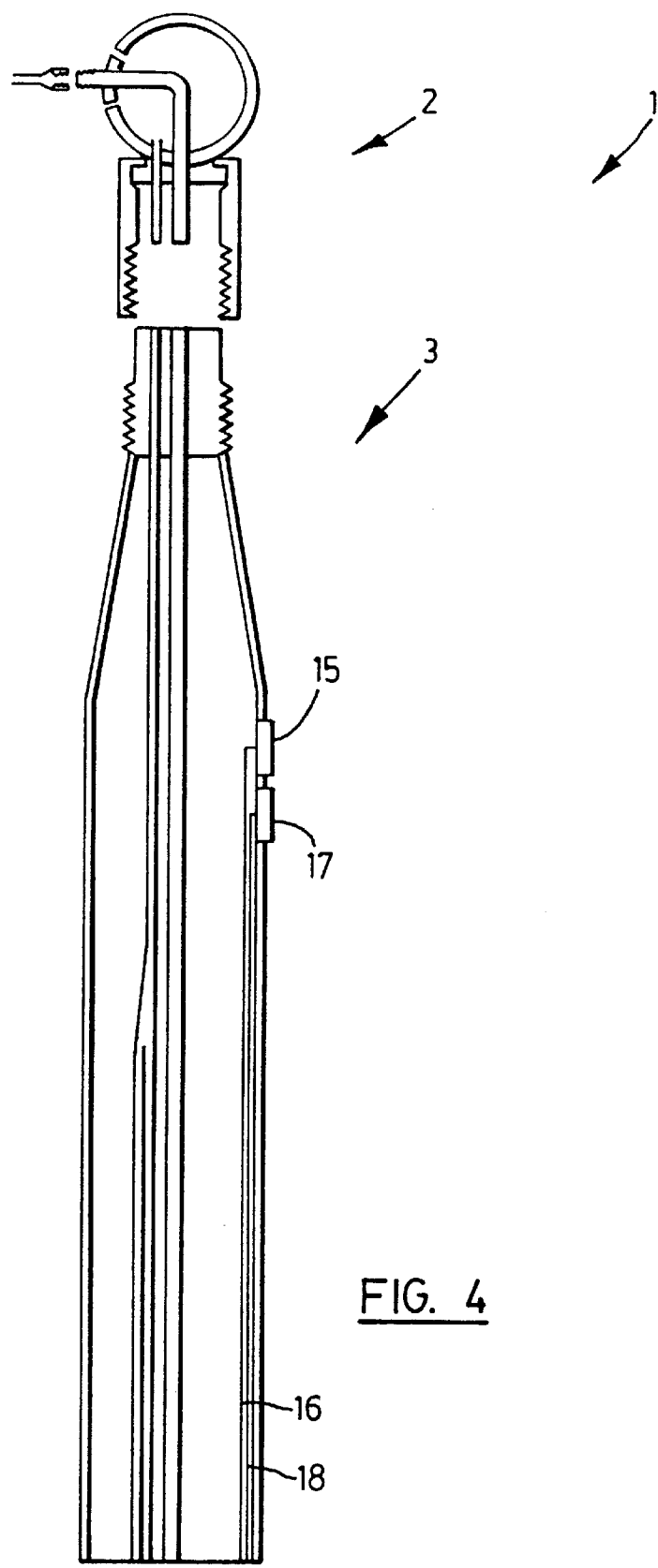
FIGS. 4 and 5 are side views of alternative dental abrading tools.
Figure 5:
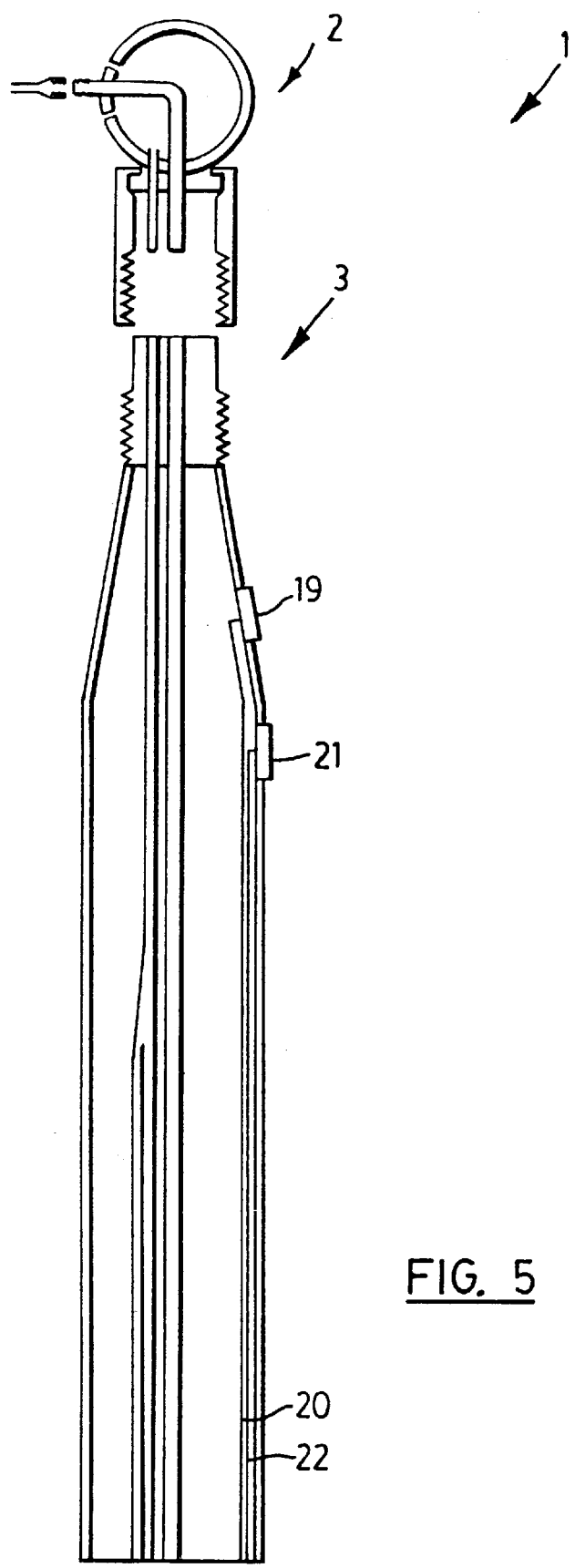

FIG. 4 illustrates an alternative in which the controlling mechanism for regulating the abrasive material stream and the analogous controlling mechanism for regulating the water-aerosol stream are push-button switches (15 and 17 respectively). These switches function in a simple on-off format Electrical line 18 supplies electricity to switch 17 and electrical line 16 supplies electricity to switch 15 In the alternative shown in FIG. 5, the controlling mechanism for regulating the abrasive material stream is a touch-control switch 19, while the touch-control switch 21 regulates the water-aerosol stream. The switches are turned on or activated when depressed. Electrical lines 20 and 22 supply power to switches 19 and 21, respectively.

Figure 6:
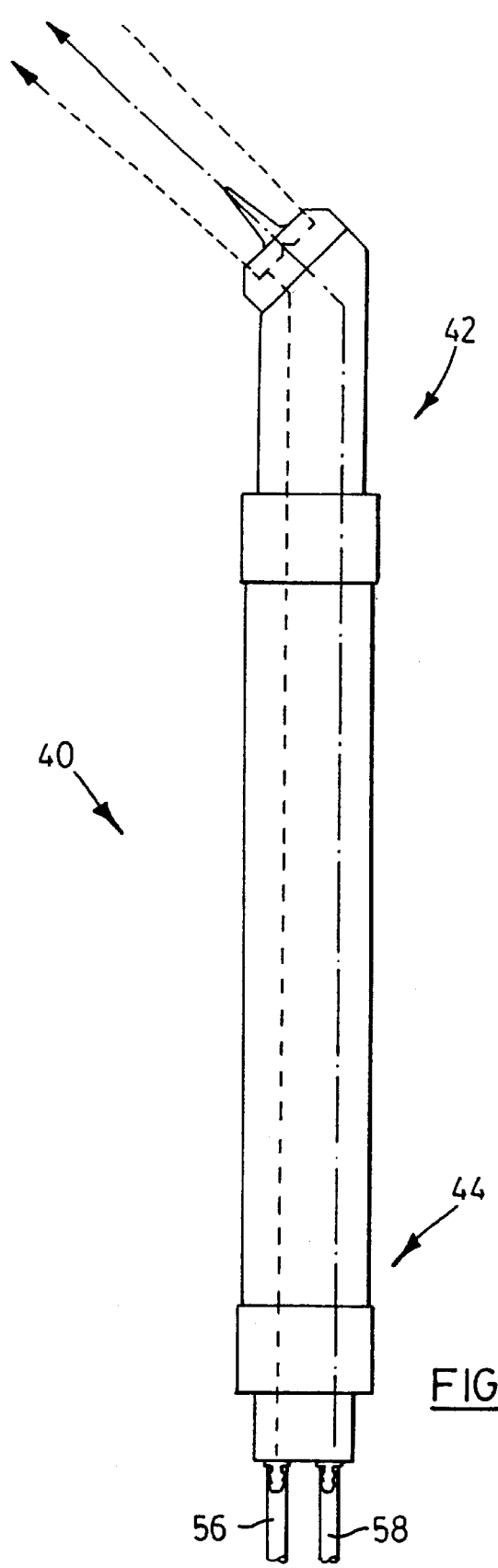
FIG. 6 is a side view of still another dental abrading tool.
Figure 7:
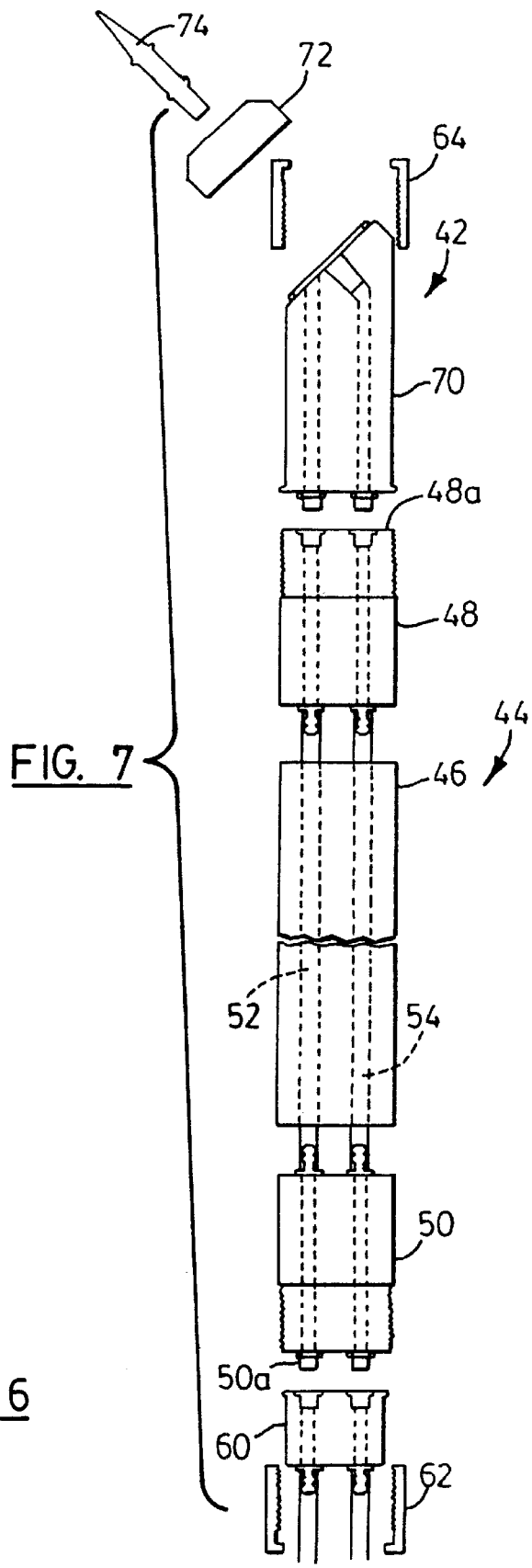
FIG. 7 is an assembly view of the tool of FIG. 6.

FIGS. 6, 7 and 7a illustrate another dental abrading tool 40. In this case, the tool 40 has a downstream nozzle portion 42 and an upstream body portion 44. The body portion has a central section 46 which is joined to two end sections 48 and 50, each defining downstream and upstream ends 48a and 50a, respectively. The upstream body portion 44 also has a pair of channels 52, 54 to receive the fluid stream and the abrasion material stream from external supply lines 56 and 58, respectively. The supply lines are suitably mounted in a connector 60 which is coupled to the upstream body section by a threaded ring 62. The channels 52, 54 extend between the downstream end 48a and the upstream end 50a The downstream end is coupled with the nozzle portion 42 by way of threaded collar 64

The nozzle portion 42 includes a main portion 70 with a nozzle body 72 threadably coupled therewith. The nozzle body also has a nozzle end piece 74 which is threadably coupled with the nozzle body.

The nozzle portion has a cavity which forms, together with the nozzle body, an inner fluids receiving chamber 76 which is open only to the channel 52 and to a number of conduits, in this cases external orifices shown at 78. Thus, fluids at the entry end of the main body travel through the channel, into the nozzle body, into the chamber and through the orifices to form a curtain which is shown by the short dashed lines at 80

The conduits may be provided in a number of configurations including slits or generally circular passages which are oriented to deliver the fluids at an angle β, as shown in FIG. 7*a*, which may range from 0 to 45 degrees, for example.

The nozzle portion also forms with the nozzle body a single passage for the abrasive material from the channel 54 through to the nozzle, thereby forming a path for the abrasive material through the channel, through the nozzle body and along the path shown by the chain dotted lines at 82. In this case, the abrasive material path is centrally located relative to the fluid paths leaving the orifices.

Referring to FIG. 7*b*, the tool 40 may from part of a dental abrasion system 90 which includes an external control portion which includes a first supply channel 92 to supply a pressurized stream of abrasion materials and a second supply channel 94 to supply a stream of pressurized fluid. In this case, the control portion may also include controls 96, 98 to adjust the variables for each stream. The first and second channels may include compressors, mixing chambers, heaters and other means for preparing and conditioning the two streams.

Figure 8A:
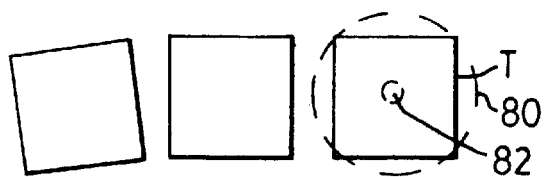
FIGS. 8a through 8e are schematic views of a dental abrading technique.
Figure 8B:
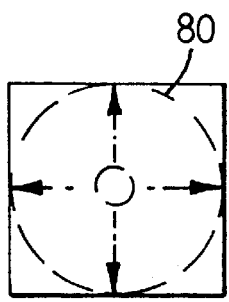

The operation of the tool is illustrated in the FIGS. 8*a* to 8*e* In FIG. 8*a*, three teeth are shown schematically by the rectangles 'T' The abrasive path is shown as the 'bullseye' of a target shown at 82 while the fluid path is shown as a relatively wider circle near the periphery of the tooth T by the dashed lines at 80. While not intending to be bound by theory, it is believed that individual abrasive materials collide with the tooth in the tooth region and assume random trajectories illustrated for example by the four compass like arrows in FIG. 8*b*, thereby toward the fluid curtain at the circle 80

Figure 8C:
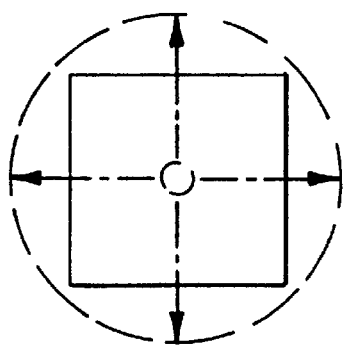
Figure 8D:
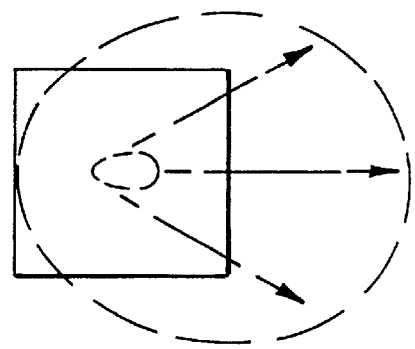
Figure 8E:
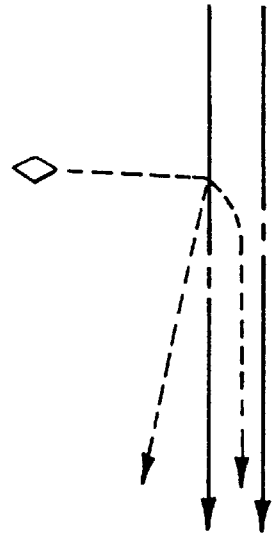

If desired, the curtain 80 may be larger than the periphery of the tooth as shown by FIG. 8*c* may take on an ellipsoid like pattern relative to the tooth, as for example might occur if the dental tool is positioned at a smaller angle relative to the tooth In this latter case, the trajectories of the abrasive materials is shown generally in the right hand direction The curtain is in fact a convergence of fluid flows from the individual orifices 78, in this particular example. The fluid will have a momentum which will be dependent on the proportion of the fluid which is a relatively dense material such as water. The greater the proportion of water in the fluid stream, the greater the chance that the approaching abrasion material particle with collide with or become entrained with an individual droplet in the fluid This may cause the particle to be repelled back toward the tooth region and thus remain airborne or otherwise be entrained in the fluid.

While the technique may not in some cases have the capability to inhibit each and every abrasion particle from actually penetrating the curtain, passing through it and remaining airborne on outside the curtain, it is believed that the technique can be adjusted to provide very high recapture rate In those cases where the abrasive particles do successfully pass through the curtain, such liberated particles should have lost a significant portion of its energy, thereby reducing its capacity to damage or otherwise penetrate tissues near the tooth region and outside the curtain The abrasive material thus becomes entrained in the fluids or the saliva of the patient or both which can subsequently be removed by conventional suction techniques.

While not intending to be bound by theory, there are believed to be several variables that are interdependent and changes to them may have positive, for that matter negative, effects on the ability for the system to suppress airborne abrasion materials. For example, increasing the liquid content of the fluid supply, such as water for example, may improve the dust suppression ability of the fluid, as will an increase in the fluid pressure. An increase in the beam intensity (that is the pressure at which the abrasion material is delivered to the nozzle) may reduce the effectiveness of the fluid curtain, simply because the airborne abrasion materials may penetrate the curtain with a greater speed, for example. An increasing content of liquid in the fluid may increasingly impair or obstruct the dental health professional's view of the target region. Therefore, it may be desirable in some cases to permit the professional to adjust these variables at his discretion, to allow the system to suppress the airborne abrasive material to a degree deemed satisfactory by the professional while at the same time allowing the dentist sufficient viewing of the target region with a suitable beam intensity.

It will understood by those skilled in the art that the device should be prepared in a manner suitable for its intended used This may include, for example, fabricating the device from autoclavable materials or those which are capable to be sterilized by other techniques It may also be appropriate in some cases to provide the tool as a disposable article.

While the above system makes use of a tool which supplies both an abrasive material stream and a fluid stream capable of establishing a barrier for suppressing airborne abrasive material, the system may alternatively be arranged wherein the abrasive material is supplied by one tool and the barrier-forming fluid stream supplied by another implement.

The terms 'suppress' and 'barrier' are intended not to limit the invention necessarily to only those cases where the suppression and barriers are absolute Rather, these terms are intended to include cases where the suppression and barriers may only function to prevent a portion of the airborne abrasive material from leaving the tooth region For example, there may be significant benefit to be gained by preventing, for example, 90 percent of the airborne abrasion materials from leaving the tooth region.

The device is also convenient because the curtain can be arranged to provide improved suppression without significantly blocking the dental professional's view of the tooth region.

While the curtain shown above completely encircles the tooth region, there may be cases where the fluid need not form a complete circumferential barrier. For example, there maybe some cases where the fluid barrier cooperates with a physical barrier, the latter being, for example behind the tooth region and there is in a position not to impair the professional's view of the tooth region, for example The foregoing description of some embodiments of the invention should be considered as merely illustrative of the principles of the invention. Further, since numerous modifications and changes will readily occur to those skilled in the art, it is not desired to limit the invention to the exact construction and operation shown and described. Accordingly, all suitable modifications and equivalents may be resorted to, and are considered as falling within the scope of the invention.

What I claim is:

1. A dental abrasion device comprising:
   first delivery means for delivering pressurized abrasive material to a tooth region;
   supply means for supplying a pressurized aerosol mixture of a gas and a liquid; and
   second delivery means for delivering said aerosol mixture near said tooth region under conditions sufficient to suppress airborne emissions of said abrasive material from said tooth region.

2. A device as defined in claim 1 wherein said first delivery means includes a head and a nozzle mounted on the head with a first conduit in the nozzle to supply said abrasive material.

3. A device as defined in claim 2 wherein said second delivery means includes at least a plurality of second conduits near said first conduit to supply said pressurized aerosol mixture.

4. A device as defined in claim 3 wherein the second conduits are symmetrically spaced relative to a central axis.

5. A device as defined in claim 4 wherein said first conduit is centrally located relative to said second conduits.

6. A device as defined in claim 5 wherein said second conduits are configured so that individual streams leaving said second conduits converge to a substantially continuous spray of the pressurized aerosol mixture towards said tooth region.

7. A device as defined in claim 6 wherein said spray defines an inner region, said first conduit being arranged to deliver the abrasive material to said inner region.

8. A device as defined in claim 2 wherein the nozzle is mounted on a face plate, said delivery means includes cavity adjacent said face plate, the face plate having a plurality of openings through which the pressurized aerosol mixture is emitted to form a curtain for suppressing emissions of airborne abrasive material.

9. A method as defined in claim 8 wherein the abrasive material is either water soluble or water insoluble.

10. A device as defined in claim 1 wherein said liquid includes water.

11. A device as defined in claim 1 wherein said gas includes air, carbon dioxide or nitrogen.

12. A device as defined in claim 1 wherein the supply means is operable to provide the pressurized aerosol mixture with a water content ranging from 10 to 75 percent water by volume.

13. A device as defined in claim 12 wherein the supply means is operable to provide the pressurized aerosol mixture with a water content ranging from 25 to 65 percent water by volume.

14. A device as defined in claim 1 wherein the supply means is operable to provide the pressurized aerosol mixture with an air pressure ranging from about 5 psi to 75 psi.

15. A device as defined in claim 1 wherein the supply means for supplying a pressurized aerosol mixture of air and water includes a mixing chamber for receiving air and water and for preparing the pressurized aerosol mixture.

16. A device as defined in claim 15, wherein the supply means includes a heater for heating the pressurized aerosol mixture.

17. A device as defined in claim 1 wherein the supply means for supplying a pressurized aerosol mixture of a gas and a liquid includes a mixing chamber, a first supply channel to deliver the liquid the mixing chamber and a second supply channel to deliver the gas to the mixing chamber.

18. A dental abrasion device comprising first delivery means for delivering abrasive material to a tooth region, supply means for supplying a pressurized aerosol mixture of a gas and a liquid and second delivery means for delivering a pressurized aerosol mixture toward said tooth region under suitable conditions for retarding the escape of airborne abrasive material from said tooth region.

19. A device as defined in claim 18 and which is operable to form a curtain from the pressurized aerosol mixture around the tooth region.

20. A device as defined in claim 18 and which is operable to form a curtain from the pressurized aerosol mixture which encircles the tooth region.

21. A device as defined in claim 18 wherein said first delivery means includes a head and a nozzle mounted on the head with a first conduit therein to receive said abrasive material and said second delivery means includes at least a plurality of second conduits near said first conduit to receive said pressurized aerosol mixture.

22. A device as defined in claim 18 wherein said fluid is water.

23. A device as defined in claim 22 wherein said gas is air.

24. A device as defined in claim 18 wherein said second delivery means is operable to deliver the pressurized aerosol mixture which includes 10 to 75 percent water by volume.

25. A device as defined in claim 24 wherein the pressurized aerosol mixture includes 25 to 65 percent water by volume.

26. A dental abrasion tool comprising a head, a nozzle mounted on the head which is further connectable to a supply of abrasive material, supply means for supplying a pressurized aerosol mixture of a gas and a liquid, means for the delivery of the pressurized aerosol mixture of a gas and a liquid to the head and at least one outlet at the head adjacent the nozzle to emit said pressurized aerosol mixture, thereby constituting means for suppressing abrasive material dust.

27. The tool of claim 26 in which the head is detachable.

28. The tool of claim 26 in which the head further comprises an adjustable swivel mechanism allowing for the movement of the nozzle of the head to a plurality of positions.

29. The tool of claim 26 to which a detachable nozzle is further attached to the nozzle of the head.

30. The tool of claim 26 further comprising a hand piece and a control unit.

31. The tool of claim 30 in which the hand piece and the control unit are combined in a single unit.

32. The tool of claim 31 in which the head forms part of the hand piece.

33. The tool of claim 31 in which the hand piece further comprises:
   a) a first passage for passing the abrasive material through the hand piece, said first passage being in communication with said nozzle, whereby said abrasive material stream is emitted through the nozzle on the head;
   b) a cavity for receiving the pressurized aerosol mixture and a second passage for delivering the pressurized aerosol mixture through the hand piece, said second passage being in communication with said cavity to deliver said pressurized aerosol mixture thereto
   and wherein the cavity has a plurality of outlets for delivering the pressurized aerosol mixture.

34. The control unit of claim 33, further comprising a means for regulating at least one aspect of the dental abrasion tool selected from liquid pressure, gas pressure, abrasive stream composition, and abrasive material stream intensity.

35. A method of abrading a tooth, comprising the steps of:
   delivering a first supply of abrasive material to a tooth region in a patient's oral cavity; and
   delivering a second supply of pressurized aerosol mixture of a gas and a liquid toward said tooth region, wherein said aerosol mixture has sufficient volume and pressure to form a barrier to airborne abrasive material between said tooth region and said oral cavity.

36. A method as defined in claim 35 wherein the step of delivering a first supply of abrasive material includes the steps of:
   providing a head and a nozzle mounted on the head; and
   providing a first central conduit therein to supply said abrasive material.

37. A method as defined in claim 36 wherein the step of delivering a second supply of a pressurized aerosol mixture includes the step of providing a plurality of second conduits near said first conduit to deliver said pressurized aerosol mixture.

38. A method as defined in claim 34, further comprising the step of configuring the second conduits so that the pressurized aerosol mixture forms a spray toward a target region of the tooth.

39. A method as defined in claim 38, further including the step of spacing the second conduits symmetrically relative to a central axis of the nozzle.

40. A method as defied in claim 39, further including the step of positioning the first conduit centrally relative to the second conduits.

41. A method as defined in claim 39 further comprising the step of configuring the second conduits so that individual streams leaving the second conduits converge to a substantially continuous curtain.

42. A method as defined in claim 41 further comprising the step of delivering the abrasive material to a region within said curtain, in a manner uninterrupted by the pressurized aerosol mixture.

43. A method as defined in claim 35 wherein the gas includes air, carbon dioxide or nitrogen.

44. A method as defined in claim 35 wherein the pressurized aerosol mixture has a water content ranging from 10 to 75 percent by volume.

45. A method as defined in claim 44 wherein the water content ranges from 25 to 65 percent by volume.

46. A method as defined in claim 44 wherein the pressurized aerosol mixture is at a pressure ranging from about 5 psi to 75 psi.

47. A method as defined in claim 35, further comprising the step of configuring the pressurized aerosol mixture to form a curtain around the tooth region.

48. A dental system comprising a hand tool and a supply means operable to deliver an abrasive material stream and a fluid stream including a pressurized aerosol mixture of a gas and a liquid to the hand tool under conditions sufficient to deliver an abrasive material to a tooth region while forming a curtain to suppress airborne abrasive material emissions from said tooth region.

49. A system as defined in claim 48, wherein the tool has a head and a nozzle mounted on the head with a first conduit therein to supply said abrasive material.

50. A system as defined in claim 49 wherein the tool further comprises a plurality of second conduits near said first conduit to supply said fluid stream.

51. A system as defined in claim 50 wherein the second conduits are spaced relative to a central axis.

52. A system as defined in claim 51 wherein said first conduit is centrally located relative to said second conduits.

53. A system as defined in claim 52 wherein said second conduits are configured so that individual streams leaving said second conduits converge to a substantially continuous spray towards said tooth region.

54. A system as defined in claim 53 wherein said spray defines an inner region, said first conduit being arranged to deliver said abrasive material to said inner region.

55. A system as defined in claim 54 wherein said aerosol mixture is a mixture including a gas and a liquid.

56. A system as defined in claim 55 wherein said gas includes air, carbon dioxide or nitrogen.

57. A system as defined in claim 55 wherein the liquid includes water.

58. A method of abrading a tooth, comprising:
   a step for delivering first supply of abrasive material to a tooth region in a patient's oral cavity; and
   a step for delivering a second supply of a pressurized aerosol mixture of air and water near said tooth region, wherein said fluid has sufficient volume and pressure to form a barrier to airborne abrasive material between said tooth region and said oral cavity.

59. A method as defined in claim 58 further comprising the step of delivering the pressurized aerosol mixture as a curtain around the tooth region.

60. A method of abrading a tooth, comprising the steps of:
   preparing a first supply of abrasive material;
   delivering the first supply of abrasive material to a tooth region in a patient's oral cavity;
   preparing a second supply of a pressurized aerosol mixture of air and water; and
   delivering said pressurized aerosol mixture near said tooth region, wherein said pressurized aerosol mixture has sufficient volume and pressure to form a curtain, thereby to form a barrier to airborne abrasive material between said tooth region and said oral cavity.

61. A method as defined in claim 60 further comprising the steps of:
   providing a first conduit for delivering the abrasive material to the tooth region; and
   providing at least one second conduit for directing the pressurized aerosol mixture toward the tooth region.

62. A method as defined in claim 61, further comprising the step of orienting the second conduit in order to position said curtain beyond a perimeter region of the tooth region.

63. A dental abrasion device comprising first delivery means to deliver abrasive material to a tooth region, supply means for supplying a pressurized aerosol mixture of a gas and a liquid, and second delivery meant to deliver the supply of a pressurized aerosol mixture of a drive gas and a liquid near said tooth region and in the form of a curtain surrounding the tooth region, under suitable conditions to provide uninterrupted passage of the abrasive material to the tooth region for contact therewith and to retard abrasive particles deflecting from the tooth region from passing through the curtain.

64. A device as defined in claim 63 further comprising control means for operating said device:
   a) with the abrasive material being delivered to the tooth region without the pressurized aerosol mixture;
   b) with the pressurized aerosol mixture being delivered to the tooth region without the abrasive material;
   c) with the abrasive material and the pressurized aerosol mixture being simultaneously delivered to the tooth region and
   d) when neither the abrasive material nor the pressurized aerosol mixture are delivered to the tooth region.

65. A dental prophylaxis method, comprising the steps of:
delivering an abrasive material to a tooth region under conditions sufficient to condition the tooth region;
providing a pressurized drive gas;
mixing water with the pressurized drive gas in order to form a pressurized aerosol mixture;
delivering the pressurized aerosol mixture to the tooth region, under conditions sufficient to cause the pressurised aerosol mixture to form a curtain around the tooth region to impede the passage of airborne abrasive material away from the tooth region.

66. A method as defined in claim 65 wherein the pressurized aerosol mixture has a water content ranging from 10 to 75 percent, by volume.

67. A method as defined in claim 66 wherein the water content ranges from 25 to 65 percent by volume.

68. A method as defined in claim 65 wherein the drive gas is at a supply pressure of 5 psi to 75 psi.

69. A method as defined in claim 65 further comprising the step of orienting curtain at an angle ranging from 0 to 45 degrees relative to a central axis of the nozzle.

* * * * *